United States Patent [19]
Ozker et al.

[11] Patent Number: 6,099,822
[45] Date of Patent: Aug. 8, 2000

[54] IMAGING METHODS AND COMPOSITIONS

[76] Inventors: Suleyman Kutlan Ozker, 2320 Buckingham Pl., Brookfield, Wis. 53045; Bert David Collier, 621 N. 77th St., Milwaukee, Wis. 53213

[21] Appl. No.: 09/146,785

[22] Filed: Sep. 3, 1998

Related U.S. Application Data

[60] Provisional application No. 60/058,171, Sep. 5, 1997.
[51] Int. Cl.$^7$ ............................ A61K 51/00; A61M 36/14
[52] U.S. Cl. ...................... 424/1.73; 424/1.11; 424/9.1; 424/1.65; 127/30; 127/36; 514/23
[58] Field of Search ................... 424/1.11, 1.65, 424/1.73, 1.37, 9.1, 9.3, 9.4, 9.5, 9.6, 9.7; 127/30, 36; 252/381; 534/10–16; 206/223, 569, 570; 514/23; 436/95

[56] References Cited

U.S. PATENT DOCUMENTS

| | | | |
|---|---|---|---|
| 3,466,361 | 9/1969 | Richards et al. | 424/1.11 |
| 4,208,398 | 6/1980 | Kubiatowicz et al. | |

OTHER PUBLICATIONS

U. Abram, et al., "Technetium Mixed–Ligand Complexes Containing Bidentate Phosphines and Monodentate Tiol Ligands. Preparation, in vitro Data and Detection of a Certain Heart Affinity," *Appl. Radiat. Isol.* 39(5):385–390, 1988.

A.M. Markoe, et al., "Tissue Distribution and Retention of 5–thio–D–glucose in Animal Tumor Models," *Canc. Clin. Trials* 3(2):155–163, 1980 (Abstract).

K. Ozker, et al., "Tc–99m Labeled 5–thio–D–glucose," *J. Nucl. Med.* 39(5) :217P, 1998 (Abstract).

Dox et al, The Harper Collins Illustrated Medical Dictionary, pp. 227 (ischemia & ischemic) & 494 (tumor), 1993.

*Primary Examiner*—Jose' G. Dees
*Assistant Examiner*—Dameron Jones
*Attorney, Agent, or Firm*—Quarles & Brady LLP

[57] ABSTRACT

Disclosed is a composition of matter useful in imaging tissue, the composition comprising a complex formed between technetium (Tc-99m) and 5-thio-D-glucose. Also disclosed is a method of in vivo imaging of acute ischemic tissue and tumors in a mammalian subject comprising delivering into the subject an effective amount of (Tc-99m)-5-thio-D-glucose, and scanning the subject to determine the distribution of the Tc-99m-TG complex in the subject. A method of preparing the composition of matter is also disclosed.

19 Claims, No Drawings

IMAGING METHODS AND COMPOSITIONS

CROSS-REFERENCE TO RELATED APPLICATION

This application claims priority to U.S. Provisional Application Ser. No. 60/058,171, filed Sep. 5, 1997. This application is hereby incorporated by reference.

STATEMENT REGARDING FEDERALLY SPONSORED RESEARCH OR DEVELOPMENT

Not applicable.

BACKGROUND OF THE INVENTION

The prognosis of patients suffering myocardial infarction or malignant tumors depends on early diagnosis and intervention. Therefore, medical practitioners wish to obtain improved imaging methods to facilitate early, accurate diagnosis of serious health conditions, such as myocardial infarcts and tumors.

Previous reports suggest that various glucose analogs (glucoheptonate, gluconate, glucarate) labeled with Tc-99m may be useful for the detection of tumors and acute tissue injury [1–8]. More recently, Tc-99m-labeled glucarate, a six carbon dicaroxylate sugar, was found to accumulate in both experimental tumors and in acute myocardial infarction [9–12].

In several clinical and preclinical investigations, Tc-99m-glucarate has recently been documented to be preferentially retained by necrotic tissue [10–12]. Tc-99m-glucarate localization was significantly greater in necrotic cells compared to normal control cells and ischemic viable cells [11]. It has been suggested that this agent may be useful in the early detection of necrotic myocardium and differentiation from ischemic myocardium in patients with acute onset of chest pain [10, 12].

The exact mechanism of Tc-99m-glucarate localization is currently not known. However, it was shown in a cell culture system that presence of fructose reduced the accumulation of Tc-99m-glucarate in hypoxic cells but had no effect on accumulation in aerobic cells [3, 13]. A proposed mechanism of uptake is based on decreased availability of oxygen causing an increased extraction of Tc-99m-glucarate in tumor and ischemic tissues via an anaerobic pathway [13].

Ballinger, et al. reported that under hypoxia, the presence of fructose reduced the accumulation of Tc-99m-glucarate by 30% and Tc-99m-gluconate by 40% in Chinese hamster ovary cells, but had no significant effect on accumulation of these Tc-99m-labeled carbohydrates in aerobic conditions [13]. Based on these observations, together with the exclusion of Tc-99m-DTPA by hypoxic cells, these authors suggested that cell membranes were intact and intracellular uptake of Tc-99m-glucarate and Tc-99m-gluconate was related to fructose transport.

Recently, Petrov, et al. reported that Tc-99m-glucarate uptake in a BT-20 human breast tumor model at 5 hours (1.13% ID/g) and at 8 hours (1.21% ID/g) was significantly greater than uptake of Tc-99m-MIBI and Tc-99m-DTPA [9]. They also showed that 50.9% of the intracellular Tc-99m-glucarate accumulated in the nuclei, 34.3% in the cytoplasm, and 14.8% in the mitochondria of the tumor cells.

Orlandi, et al. reported a high affinity binding of Tc-99m-glucarate to necrotic myocardium in dogs with experimental myocardial infarction [8]. However, they found no accumulation of Tc-99m-glucarate in hypoxic but viable myocardium. Likewise, Yaoita, et al. found marked uptake of Tc-99m-glucarate in acute cerebral injury but no uptake in viable tissue [7]. Tc-99m-glucarate concentrated in the center of the cerebral injury while F-18-FDG was decreased in this region. The disparity between distribution of F-18-FDG and Tc-99m-glucarate was interpreted as evidence that Tc-99m-glucarate does not behave as a glucose analog.

Despite promise as possible imaging agents, Tc-99m-glucurate and other Tc-99m-labeled glucose analogs known to the art suffer the disadvantage of unstable Tc-99m labeling. In fact, Tc-99m labeled gluconate and glucarate are used as Tc-99m donor substrates in transchelation reactions to label antibodies and peptides [16,17]. Currently, kits containing Tc-99m-labeled gluconate or glucarate are used in transchelation reactions to label polypeptides. Reduced Tc-99m is transferred to various ligands such as antibodies and peptides from Tc-99m-labeled gluconate or glucarate due to the relatively low binding affinity of Tc-99m for these carbohydrate molecules. The potential for in vivo transfer of Tc-99m from Tc-99m-labeled gluconate or glucarate to polypeptides calls into question the advisability of using Tc-99m-labeled gluconate or glucarate in tissue imaging, because labeling of proteins by Tc-99m may interfere with the normal functioning of the proteins.

Technetium-labeled complexes containing water-soluble mercaptans for use in kidney imaging were disclosed in U.S. Pat. No. 4,208,398.

There is a need for methods and compositions for imaging tumors and acute ischemic tissue injury in humans, and methods that allow recent acute injuries to tissue, such as those caused to heart tissue by recent heart attacks, to be distinguished from normal tissue and older injuries.

BRIEF SUMMARY OF THE INVENTION

We have discovered that it is possible to distinguish between acute ischemic tissue injury and normal tissue or older injuries by a method which comprises administering intravenously to a patient an effective amount of a complex of 5-thio-D-glucose and technetium-99m (Tc-99m-5-thioglucose) and then scanning the patient using a high-speed gamma camera or similar instrument. More of the 5-thio-D-glucose technetium-99m complex may be taken up by the recently injured ischemic tissue than is taken up by normal or older injured tissue; therefore, it is possible to clearly identify and see the acute ischemic injured tissue.

The complex of the present invention can be preferably prepared by dissolving 10 mg of 5-thio-D-glucose in 1 ml of saline with low dissolved oxygen in a 10 ml vial, adding 0.01–2.0 mg of stannous chloride as a stannous ion source and then lyophilizing the mixture to form a readily reconstitutable solid. If desired, an antioxidant, such as gentisic acid, can be included in the mixture to be lyophilized. At the time of use, the lyophilized solid in the vial is reconstituted with up to 3700 MBq [$^{99m}$Tc] pertechnetate in 1–3 ml of isotonic saline to form the desired 5-thioglucose and Tc-99m complex. 370–740 MBq of the complex containing solution is then injected intravenously into a patient, and the patient is scanned with a gamma camera. As previously described, any acute ischemic tissue present is expected to take up more of the complex than the normal or older injured tissue so that it can be readily distinguished.

We also have discovered that the Tc-99m-5-thio-glucose complex is preferentially taken up by tumor tissue. Therefore, the complex also can be used to help identify and locate tumors.

The advantages of our invention over previous methods for imaging acute ischemic tissue and tumors will be apparent to those skilled in the art.

In one aspect, the present invention is a composition of matter for imaging tissue comprising technetium-99m (Tc-99m)-labeled 5-thio-D-glucose (Tc-99m-TG).

Another aspect of the invention is a method for labeling 5-thio-D-glucose with Tc-99m comprising combining 5-thio-D-glucose and stannous ions with a solution comprising Tc-99m and a pharmaceutically acceptable solvent.

Another aspect of the present invention is a method of imaging tissue in a mammalian subject comprising the steps of delivering into the subject an effective amount of Tc-99m-TG and scanning the subject to determine the distribution of Tc-99m-TG in the subject.

The present invention is also a kit comprising 5-thio-D-glucose and stannous ions.

It is an object of the present invention to provide a method of in vivo tissue imaging that will facilitate detection and treatment of pathological conditions including, for example, acute ischemic tissue and tumors.

It is an object of the present invention to provide a composition of matter for in vivo use in tissue imaging.

The composition of matter of the present invention has the advantages of being stable and being readily cleared from plasma and urine.

Other objects, features, and advantages of the present invention will become apparent upon review of the specification and claims.

DETAILED DESCRIPTION OF THE INVENTION

The present invention is a method of imaging tissue in vivo in a mammalian subject comprising the steps of: (a) delivering into the subject an effective amount of a complex comprising Tc-99m-labeled 5-thio-D-glucose; and (b) scanning the subject to determine distribution of the complex of step a within the subject.

There are several important factors to be considered in the design and development of imaging agents. The agent should be differentially distributed between normal cells and diseased cells, or cells associated with a disease state. A suitable imaging agent should be relatively stable, in that it should not react extensively with biochemicals found in the body. Furthermore, suitable imaging agents should be readily eliminated from the body.

The stability of a Tc-99m-labeled glucose analog can be significantly improved by labeling via a thio substitute. Among glucose analogs, 5-thio-D-glucose is the most closely related analog of D-glucose [14]. Over the years, 5-thio-D-glucose has provided a useful tool in studying the biochemistry of the parent D-glucose molecule, because the presence of the 5-thio group does not affect the biochemistry of the molecule.

The Examples detail the preparation with high labeling efficiency of a Tc-99m-labeled 5-thio-D-glucose (Tc-99m-5TG) complex using stannous ion reduction [15]. The Tc-99m-5TG complex thus prepared was found to exhibit high stability. Stability is measured by the percentage of 5TG that is labeled with Tc-99m after 24 hours from the time that the complex was prepared. Preferably, at least 90% of the 5TG is labeled with Tc-99m after 24 hours. Most preferably, at least 95% or even as much as 98% of the 5TG is labeled with Tc-99m after 24 hours.

The complex of the present invention is prepared by dissolving 5-thio-D-glucose in a suitable solvent such as normal saline (0.85 M NaCl) with low dissolved oxygen, adding a stannous ion source such as stannous chloride or stannous tin, for example, and lyophilizing the mixture to form a solid that can be conveniently stored and readily reconstituted when needed. Preferably, 10 mg 5-thio-D-glucose and 74 µg stannous ion are present. Optionally, an antioxidant such as gentisic acid can be included in the mixture to be lyophilized.

Stannous tin and stannous chloride are shown in the Examples to be suitable for the preparation of Tc-99m-5TG. It is expected that other stannous ion sources will be equally suitable for the practice of this invention.

At the time of use, the lyophilized solid is reconstituted with between 185 and 370 MBq [$^{99m}$Tc] pertechnetate in isotonic saline per milligram 5-thio-D-glucose to form the desired 5-thioglucose and Tc-99m complex. It is anticipated that any pharmaceutically acceptable carrier in which the complex is soluble may be used in the present invention. One of skill in the art would recognize that one could prepare the Tc-99m-labeled 5TG by combining a solution of 5-TG and stannous ions together with a solution of Tc-99m without first lyophilizing the 5-TG and stannous ion solution.

In the examples below, a preparation of Tc-99m-labeled 5TG was prepared by reconstituting lyophilized 5-TG and stannous ions with a Tc-99m solution and incubating the mixture at room temperature for 30 minutes prior to chromatography analysis. It is reasonably expected that Tc-99m-labeled 5TG could be prepared using shorter or longer periods of incubation. Preferably, to insure high efficiency of labeling, the incubation should be at least 10 minutes long.

To image tumors in mice, a volume of Tc-99m-T5G solution sufficient to deliver between about 9 to 10 MBq of Tc-99m-TG/kg body weight was injected intravenously into the mice. With humans, we anticipate that injection of a volume of Tc-99m-5TG solution containing about 370–740 MBq into the patient to be imaged (5 to 10 MBq/kg body weight) will be suitable for imaging tissue in the patient. Preferably, the scanning agent is administered intravenously no more than 3 hours after preparation. The subject is then scanned. Preferably, scanning is conducted between 1 and 6 hours after administration.

The Examples below describe the biodistribution of Tc-99m-TG using normal rabbits and mouse tumor models intravenously injected with Tc-99m-TG. We have discovered that it is possible to distinguish between acute ischemic tissue injury and normal tissue or older injuries by a method which comprises administering intravenously to a subject an effective amount of a complex of 5-thio-D-glucose and Tc-99m and then scanning the subject using a high-speed gamma camera or similar instrument. More of the 5-thio-D-glucose-Tc-99m complex is taken up by the recently injured ischemic tissue than normal tissue; therefore, it is possible to clearly identify and visualize the acute ischemic injured tissue. The Tc-99m-5-thio-glucose complex was found to be preferentially taken up by tumor tissue. Therefore, the complex also can be used to help identify and locate tumors.

It is reasonably expected that the methods and composition of matter of the present invention can be effectively employed with any mammalian species, including humans.

The following nonlimiting examples are intended to be purely illustrative.

EXAMPLES

Preparation of Tc-99m-5TG

Tc-99m-TG was prepared using 74 µg stannous tin, 10 mg 5-Thio-D-glucose (Aldrich Chemical Company, Milwaukee, Wis.) and 50–100 mCi (1.85–3.7 GBq) Tc-99m pertechnetate in a final volume of 2–4 mL. After a 30 minute incubation at room temperature, the solution was chromatographed using Whatman 3MM paper strips developed in methylethyl ketone (MEK) and Gelman instant thin-layer silica gel (ITLC-SG) strips developed in saline.

Labeling efficiency of Tc-99m-TG was 98.5±0.8%, stable for over 24 hours. Any unreacted Tc-99m-pertechnetate impurity present would appear at the solvent front on the chromatograms developed in MEK; insoluble Tc-99m species would appear at the origin of saline chromatogram.

The labeling reaction can be performed using the same stannous reduction method and a kit formulation having suitable ratios of 10 mg 5-thio-D-glucose and stannous ions. For example, we expect that a kit comprising about 10 mg 5-thio-D-glucose and between about 0.01 mg and 2 mg stannous ions as stannous chloride dihydrate or stannous fluoride.

Pharmacokinetic Studies of Tc-99m-5TG in Normal Rabbits

Pharmacokinetic studies were performed using male New Zealand rabbits. Following hydration with 15 ml/kg of normal saline, 20 µCi/kg (0.74 Mbq/kg) of Tc-99m-TG was injected intravenously. Arterial blood samples were obtained at 2.5, 5, 7.5, 10, 15, 30, 45, and 60 minutes after injection. Plasma samples were assayed in a NaI scintillation counter, and results were corrected for sample weight differences and radioactive decay. Urinary excretion was determined from the 60 minute urine sample and urine volume. Plasma and renal clearances were calculated using a biexponential model. Plasma protein binding was determined from 15 minute plasma samples using ultrafiltration (Ultrafree-PFL filter units, UFP2 LGC 24, Millipore Corporation, Bedford, Mass.).

Biodistribution of Tc-99m-TG in rabbits showed early and persistent accumulation in the kidneys. Plasma and renal clearance of Tc-99m-TG was 14.5±2 mL/min and 11.3±3 mL/min, respectively. A minor extra-renal (hepatobiliary) excretion accounts for this difference. Tc-99m-TG was rapidly excreted by the kidneys into the urine (53±5% at 1 hour post-injection). Protein binding was 32±0.2%. These favorable pharmacokinetic patterns of Tc-99m-TG afford high target to back-ground ratios which in turn enhances lesion detection.

Pharmacokinetic Studies of Tc-99m-5TG in Mice with Tumors

Tumor localization experiments were performed using C57BL/6 strain male mice (18–20 g) bearing MC26 colon carcinoma. 5 µCi (185 kBq) of Tc-99m-TG was injected into the tail vein of the mice. Animals were sacrificed by cervical dislocation at 1, 2 and 3 hours after injections. Tissue specimens were removed from each mouse, weighed, and counted in a NaI scintillation counter.

The biodistribution of Tc-99m-TG in mice bearing MC26 colon carcinoma was used to determine tumor localization and tumor to non-tumor ratios. Table 1 shows the concentrations of Tc-99m-TG in tumor tissue samples taken from the thigh at 1 hour and 3 hours post injection from mice bearing MC26 tumors in thigh. The Tc-99m-TG concentrations are expressed as percent uptake of injected radioactivity per gram tissue. Samples of normal muscle taken from the contralateral thigh served as a background control. Representative tumor to background ratios are also shown in Table 1. Tumor uptake of Tc-99m-TG was 1.6±0.3% at 1 hour, which decreased slightly to 1.3±0.03% and 1.2±0.3% at 2 and 3 hours post-injection, respectively. Despite a slight decrease in the tumor concentration over time, there was a continuous increase in the tumor to muscle ratios at 1 hour (2.7:1) and 3 hours (4:1) post-injection, due to gradually decreasing background. These results indicate that acceptable target to background ratios can be achieved relatively soon after administration of the agent. The one hour uptakes of Tc-99m-TG in thyroid (0.17±0.06%) and stomach (0.46±0.13%) were low. Thyroid and stomach uptakes of Tc-99m-TG were further decreased over time to 0.05±0.02% and 0.2±0.05% respectfully. This confirms our hypothesis that Tc-99m-TG is highly stable in vivo, exhibiting minimal or no breakdown to Tc-99m-pertechnetate. The biodistribution of Tc-99m-TG in the remaining organs, expressed as percent uptake of injected dose per organ, is shown in Table 2. Kidney (2.62±0.24%) and liver (2.54±0.37%) had the greatest uptake. The uptake of Tc-99m-TG in the liver decreased over time, whereas kidney showed an increase, mimicking a renal cortical accumulation.

In mice loaded with non-radioactive D-glucose, biodistribution data using the MC26 colon cancer model showed increased concentrations of Tc-99m-5-thioglucose in the blood and body background, whereas the tumor uptake of Tc-99m-5-thioglucose was decreased by a factor of two. These findings suggest that Tc-99m-5-thioglucose uptake is related to D-glucose transport and is independent of variations in blood concentrations.

TABLE 1

Localization of Tc-99m-TG as a Percentage of Injected Dose Per Gram (% ID/g) of Tumor Tissue. Values are mean % ID/g and standard deviation of the mean (n = 5).

| Tissue | 1 Hour | 2 Hours | 3 Hours |
| --- | --- | --- | --- |
| Tumor | 1.6 ± 0.3 | 1.4 ± 0.1 | 1.2 ± 0.3 |
| Muscle | 0.6 ± 0.1 | 0.5 ± 0.1 | 0.3 ± 0.1 |
| Tm/Mus | 2.7/1 | 2.8/1 | 4.0/1 |

Localization of Tc-99m-TG and $C^{14}$-2-deoxyglucose ($C^{14}$-DG) in MX-1 Tumors In order to better understand the pattern of Tc-99m-TG localization in tumors, autoradiographic biodistribution of Tc-99m-TG was compared to $C^{14}$-DG in nude mice (18–20 g) bearing MX-1 human breast tumor xeno-grafts. 3 mCi (111 MBq) of Tc-99m-5TG and 5 µCi (185 kBq) of $C^{14}$-DG were injected at the same time into the tail vein of the mice. Autoradiogram sections including the tumors and vital organs of the mice were obtained at 20 minutes, 1 hour, and 3 hours post injection and developed using simultaneous Tc-99m and $C^{14}$ exposures of the same sections.

The autoradiographic biodistribution of Tc-99m-TG in MX-1 breast showed a greater and more persistent tumor localization for Tc-99m-TG as compared to $C^{14}$-DG. Accumulation of both Tc-99m-TG and $C^{14}$-DG in the same tumor showed significantly different patterns. Tc-99m-TG concentrated at the center of the tumors whereas $C^{14}$-DG had decreased activity in this central area, suggesting a greater Tc-99m-TG avidity for the central area of necrosis.

TABLE 2

Biodistribution of Tc-99m-TG as a Percentage of Injected Dose Per Organ (% ID/organ) in Mice. Values are mean % ID/organ and standard deviation of the mean (n = 5).

| Tissue | 1 Hour | 2 Hours | 3 Hours |
| --- | --- | --- | --- |
| Heart | 0.17 ± 0.03 | 0.12 ± 0.01 | 0.13 ± 0.03 |
| Lungs | 0.41 ± 0.02 | 0.34 ± 0.02 | 0.29 ± 0.07 |
| Liver | 2.54 ± 0.37 | 2.33 ± 0.17 | 1.88 ± 0.77 |

TABLE 2-continued

Biodistribution of Tc-99m-TG as a Percentage of Injected Dose Per Organ (% ID/organ) in Mice. Values are mean % ID/organ and standard deviation of the mean (n = 5).

| Tissue | 1 Hour | 2 Hours | 3 Hours |
| --- | --- | --- | --- |
| Kidneys | 2.62 ± 0.24 | 2.43 ± 0.20 | 2.95 ± 0.49 |
| Stomach | 0.46 ± 0.13 | — | 0.20 ± 0.05 |
| Thyroid | 0.17 ± 0.06 | — | 0.05 ± 0.02 |

The findings reported herein provide evidence that Tc-99m-TG is useful as an imaging agent, and its use in imaging will facilitate therapy planning and predicting tumor response to treatment. Accumulation of Tc-99m-TG in central necrotic zone of tumors closely parallels the Tc-99m-glucorate distribution in central necrotic regions of myocardial infarcts and acute cerebral injuries as described by Orlandi, et al. [8] and Yaoita, et al. [7] respectively. This data indicates a clear discordance between the tumor localizations of Tc-99m-5-thioglucose and 2-deoxyglucose, suggesting a potential for Tc-99m-5-thioglucose in the imaging of ischemic tumor tissue.

The mechanism of localization of Tc-99m-TG in tumors and ischemic injury is unknown. Tumors and ischemic tissue are regions of low oxygen tension. Decreased availability of oxygen causes an increased extraction of glucose via an anaerobic pathway. Several carbohydrate ligands labeled with Tc-99m have been reported to accumulate in tumors and hypoxic cells by sugar transport system [1–3, 9, 13]. Others have reported that Tc-99m-carbohydrate ligands were retained in necrotic but viable tissue due to their binding to mitochondrial protein, cytochrome oxidase [7, 8, 10–12]. This latter hypothetical approach requires the presence of disruption of cell membrane during necrosis. An acute infarction presents a mixture of necrotic and ischemic tissue. Therefore both hypothetical approaches involving anaerobic transport in ischemic areas and involving mitochondrial binding in necrotic cells may have a role in extraction and retention of the carbohydrate ligands in acute infarction.

We envision that a single-step kit containing a freeze-dried 5-thio-D-glucose and stannous chloride dihydrate can be efficiently produced and used for the preparation of Tc-99m-labeled 5-thio-D-glucose complex.

All publications cited in this patent application are incorporated by reference herein.

The present invention is not limited to the exemplified embodiment, but is intended to encompass all such modifications and variations as come within the scope of the following claims.

REFERENCES

1. Leveille, J., Pison, C., Karakand, Y., Lemieux, R., Vallieres, B., "Technetium-99m glucoheptonate in brain-tumor detection: An important advance in radiotracer technique," *J. Nucl. Med.* 18:957–961, 1977.
2. Pak, K. Y., Nedelman, M. A., Daddona, P. E., "Visualization of experimental tumor model: Application of a new Tc-99m labeled compound," *J. Nucl. Med.* 30:906, 1989.
3. Rivera, J., Rabito, C. A., "Transport mechanism of Tc-99m glucoheptonate by renal and lung tumor cells," *J. Nucl. Med.* 30:912, 1989.
4. Uehara, T., Ahmad, M., Khaw, B. A., Fischman, A. J., Pak, K. Y., Berger, H., Straus, H. W., "Tc-99m-glucarate: A marker of acute cerebral damage," *J. Nucl. Med.* 30:901, 1989.
5. Fornet, B., Yasuda, T., Wilkinson, R., Ahmad, M., Moore, R., Khaw, B. A., Fischman, A. J., Straus, H. W., "Detection of acute cardiac injury with technetium-99m glucaric acid," *J. Nucl. Med.* 30:1743, 1989.
6. Ohtani, H., Callahan, R. J., Khaw, B. A., Fischman, A. J., Wilkinson, R., Straus, H. W., "Comparison of Tc-99m glucarate and thallium-201 for the identification of myocardial infarction," *J. Nucl. Med.* 32:1029, 1991.
7. Yaoita, H., Uehara, T., Brownel, A. L., Rabito, C. A., Ahmad, M., Khaw, B. A., Fischman, A. J., Straus, H. W., "Localization of technetium-99m-glucarate in zones of acute cerebral injury," *J. Nucl. Med.* 32:272–278, 1991.
8. Orlandi, C., Crane, P. D., Edwards, D. S., Platts, S. H., Bernard, L., Lazewatsky, J., Thoolen, M., "Early scintigraphic detection of experimental myocardial infarction in dogs with technetium-99m-glucaric acid," *J. Nucl. Med.* 32:263–268, 1991.
9. Petrow, A. D., Narula, J., Nakazawa, A., Pak, K. Y., Khaw, B. A., "Targeting human breast tumour in xeno-grafted SCID mice with Tc-99m-glucarate," *Nucl. Med. Commun.* 18:241–251, 1997.
10. Beanlands, R. S. B., Ruddy, T. D., Bielawski, L., Johansen, H., "Differentiation of myocardial ischemia and necrosis by technetium 99m glucaric acid kinetics," *J. Nucl. Cardiol.* 4:274–282, 1997.
11. Khaw, B. A., Nakazawa, A., O'Donnell, S. M., Pak, K. Y., Narula, J. N., "Avidity of technetium 99m glucarate for the necrotic myocardium: and in vivo assessment," *J. Nucl. Cardiol.* 4:283–290, 1997.
12. Mariani, G., Villa, G., Rossettin, P. F., Motta, C., Spallarossa, P., Calcagno, G., Bezante, G. P., Taddei, G., Brunelli, C., Caponnetto, S., Straus, H. W., "Technetium-99m glucaric acid as a marker of acute myocardial necrosis: Initial imaging experience in 24 patients," *J. Nucl. Med.* 38:98P, 1997.
13. Ballinger, J. R., Cowan, D. S. M., Boxen, I., Zhang, Z. M., R, A,M., "Effect of hypoxia on the accumulation of technetium-99m-glucarate and technetium-99m-gluconate by chinese hamster ovary cells in vitro," *J. Nucl. Med.* 34:242–245, 1993.
14. Whistler, R., Lake, C. W., "Inhibition of cellular transport processes by 5-thio-D-glucopyranose," *Biochem. J.* 130:919–925, 1972.
15. Ozker, K., Collier, B. D., Lindner, D. J., Kabasakal, L., Liu, Y., Krasnow, A. Z., Hellman, B. S., Edwards, D. S., Bourque, C. B., Crane, P. D., "Tc-99m-labeled 5-thio-D-glucose," *J. Nucl. Med.* 39:217P, 1998.
16. Eckelman, W. C., Steigman, J., "Direct labeling with Tc-99m," *Nucl. Med. Biol.* 18:3–7, 1991.
17. Pak, K. Y., Nedelman, M. A., Tam, S. H., Wilson, E., Daddona, P. E., "Labeling and stability of radiolabeled antibody fragments by a direct Tc-99m-labeling method," *Nucl. Med. Biol.* 19:669–677, 1992.

We claim:

1. A method of imaging acute ischemic tissue in vivo in a mammalian subject comprising the steps of:
    (a) administering to the mammalian subject an effective amount of a complex comprising 5-thio-D-glucose and Tc-99m; and
    (b) imaging the subject to determine the distribution of the Tc-99m complex of step a in the subject wherein localization of the Tc-99m and 5-thio-D-glucose complex indicates ischemic tissue.

2. The method of claim 1 wherein the amount of complex delivered is between 5 MBq and 10 MBq per kilogram body weight of the subject.

3. The method of claim 1 wherein the subject is a human.

4. The method of claim 1 wherein the complex is administered intravenously.

5. A method of imaging a tumor in a mammalian subject comprising the steps of:
   (a) administering to the mammalian subject an effective amount of a complex comprising 5-thio-D-glucose and Tc-99m; and
   (b) imaging the subject to determine the distribution of the Tc-99m complex of step a in the subject wherein localization of the Tc-99m and 5-thio-D-glucose complex indicates a tumor.

6. The method of claim 5 wherein the amount of complex administered is between 5 MBq and 10 MBq per kilogram body weight of the subject.

7. The method of claim 5 wherein the subject is a human.

8. The method of claim 5 wherein the complex is administered intravenously.

9. A diagnostic composition of matter comprising a technetium-labeled 5-thio-D-glucose complex.

10. The composition of claim 9 wherein at least 90% of the 5-thio-D-glucose present in the composition is labeled with technetium.

11. A composition of matter comprising technetium-labeled 5-thio-D-glucose and stannous ions.

12. The composition of claim 11, wherein the composition is in the form of a lyophilized solid.

13. The composition of claim 11, wherein stannous ion is supplied as stannous chloride dihydrate or stannous flouride.

14. The composition of claim 11, wherein the composition comprises about 10 mg 5-thio-D-glucose and between about 0.01 mg and 2 mg stannous ions as stannous chloride dihydrate or stannous flouride.

15. The composition of claim 11, wherein the composition further comprises a preservative.

16. A kit comprising the composition of claim 11.

17. A method of preparing a complex of Tc-99m-labeled 5-thio-D-glucose comprising the step of combining 5-thio-D-glucose, stannous ions, and a solution of Tc-99m in a pharmaceutically acceptable solvent.

18. The method of claim 17, wherein the 5-thio-D-glucose and stannous ions are provided as the composition of claim 11.

19. The method of claim 17, wherein the Tc-99m solution comprise between 185 and 370 MBq per mg 5-thio-D-glucose.

* * * * *